United States Patent [19]

Heinz et al.

[11] Patent Number: 4,747,119
[45] Date of Patent: May 24, 1988

[54] CEILING MOUNT FOR AN X-RAY RADIATOR

[75] Inventors: Lothar Heinz, Neunkirchen; Thomas Schmitt, Forchheim, both of Fed. Rep. of Germany

[73] Assignee: Siemens Aktiengesellschaft, Berlin and Munich, Fed. Rep. of Germany

[21] Appl. No.: 843,379

[22] Filed: Mar. 24, 1986

[30] Foreign Application Priority Data

May 2, 1985 [DE] Fed. Rep. of Germany ... 8512989[U]

[51] Int. Cl.4 ............................................. H05G 1/02
[52] U.S. Cl. .................................... 378/197; 378/196; 378/198; 188/42
[58] Field of Search ...................... 378/196, 197, 198; 188/42, 43

[56] References Cited

U.S. PATENT DOCUMENTS

| 1,658,192 | 2/1928 | Hampton | 188/42 |
|---|---|---|---|
| 2,909,665 | 10/1959 | Guentner et al. | 378/194 |
| 2,924,716 | 2/1960 | Angel et al. | 378/197 |
| 3,121,793 | 2/1964 | Thomas | 378/91 |
| 3,891,856 | 6/1975 | Amor, Jr. et al. | 378/197 |

FOREIGN PATENT DOCUMENTS

| 7508074 | 8/1976 | France . | |
| 303820 | 2/1955 | Switzerland . | |
| 670239 | 4/1952 | United Kingdom . | |
| 0715568 | 9/1954 | United Kingdom | 378/197 |

OTHER PUBLICATIONS

Deckenstative fur den Anbau von Rontgenstrahler und Bildverstarker, Published 12/81.

Primary Examiner—Janice A. Howell
Assistant Examiner—David P. Porta
Attorney, Agent, or Firm—Hill, Van Santen, Steadman & Simpson

[57] ABSTRACT

The invention relates to a ceiling mount for an X-ray radiator comprising a carriage carrying said X-ray radiator, the carriage being displaceably guided in rails. For the purpose of locking the carriage, a friction block motor-displaceable perpendicular to the rail direction is attached to the carriage, this friction block being secured to a holder resiliently seated perpendicular to the rail. The holder comprises a latch facing the rail which interacts with corresponding latches on the rail of the carriage. The holder is thereby adjustable in three positions. In the first position, free mobility of the carriage is possible; in the second position, a resilient latching ensues when the latches on the rail are traversed; and in the third position, the friction block is pressed against the rail for locking the position of the carriage.

9 Claims, 1 Drawing Sheet

CEILING MOUNT FOR AN X-RAY RADIATOR

BACKGROUND OF THE INVENTION

1. Field of the Invention

The invention relates to a ceiling mount for an X-ray radiator comprising a carriage carrying the X-ray radiator, the carriage being displaceably guided in rails, whereby a motor-displaceable friction block is applied to the carriage perpendicular to the rail direction for the purpose of arresting the carriage.

2. Description of the Prior Art

FIG. 1 shows a ceiling mount of the type described above which is known in the art. An X-ray radiator 1 including a primary radiation diaphragm 2 is secured to a carriage 4 with the assistance of a telescoping carrier 3, this carriage 4 being seated longitudinally displaceable in rails 5. The rails 5 are displaceably seated in rails 7 which proceed perpendicular thereto and are secured to the ceiling 6 of the examination room, so that a two-dimensional displacement of the carriage 4 is possible. On the basis of the telescoping carrier 3, accordingly, the X-ray radiator 1 is three-dimensionally adjustable. A patient (not shown) lying on a platform can, for example, be irradiated in vertical direction with the assistance of the X-ray radiator 1.

When the X-ray radiator 1 has reached its desired position in the room, then the carriage 4 must be locked with respect to the rails 5 and the rails 5 must be locked with respect to the rails 7. It is known to provide electromagnets for this purpose, these electromagnets cooperating with strips of magnetizable material situated in the rails 5, 7.

The locking of the carriage 4 with respect to the rails 5 and of the rails 5 with respect to the rails 7 can also ensue by means of friction blocks which are motor-adjustable perpendicular to the respective rail direction. Given employment of such friction blocks, it is superfluous to provide magnetizable material in the rails guiding the carriage or to fabricate these rails of magnetizable material. Accordingly, they can be composed of aluminum channels.

The locking of the carriage usually does not ensue at arbitrary locations but, rather, in exposure locations which frequently repeat.

SUMMARY OF THE INVENTION

An object of the invention is to improve a ceiling mount of the type initially cited such that an easy locating of predetermined exposure positions is enabled upon the use of at least one friction block for locking the carriage which is motor-adjustable toward and away from the corresponding rail direction.

This object is achieved in accord with the invention in that the friction block is secured to a holder resiliently seated perpendicular to the corresponding rail, the holder comprising a latch facing the allocated rail which interacts with corresponding latches on the rail. Given the ceiling mount of the invention, it is possible to bring the friction block so close to the rail by motor-drive that the holder engages with the rail when an exposure position is reached and, thus, exactly defines the exposure position.

BRIEF DESCRIPTION OF THE DRAWINGS

The invention shall be set forth in greater detail below with reference to an exemplary embodiment shown in two view in FIGS. 2 and 3.

DESCRIPTION OF THE PREFERRED EMBODIMENTS

Figure 1:
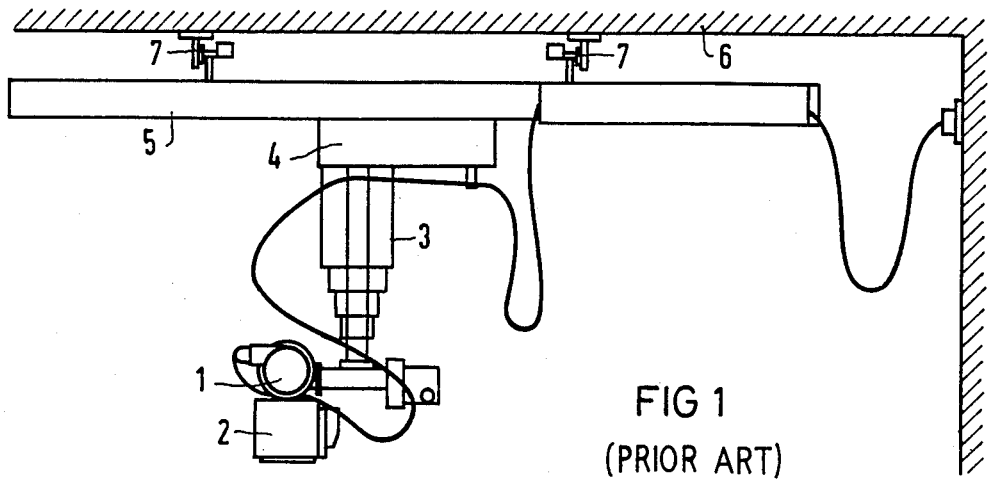
Figures 2, 3:
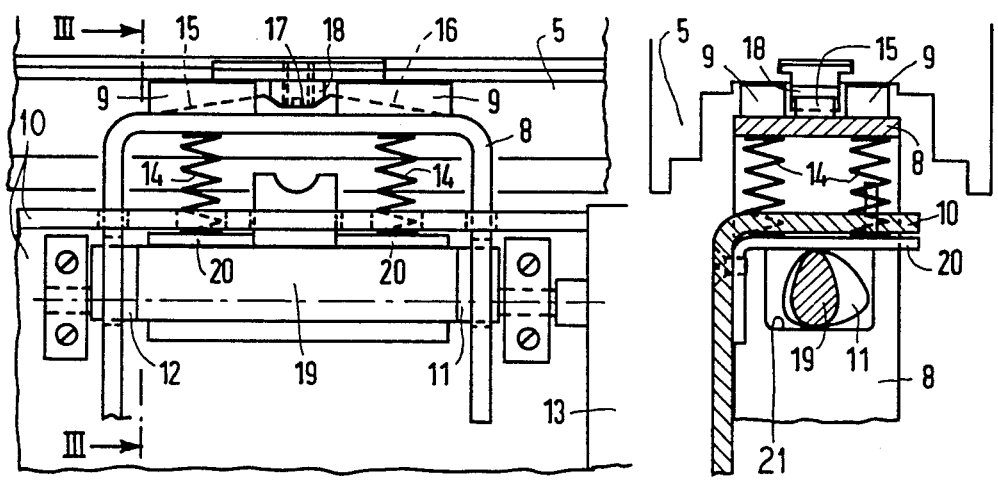
FIG. 2 is a side elevational view of the positioning apparatus of the presention invention.
FIG. 3 is a sectional view taken generally along the line III—III of FIG. 2.

FIGS. 2 and 3 show one of the rails 5 with which a friction block 9 secured to a holder 8 interacts. The holder 8 is thereby guided in a guide 10 and is displaceable perpendicular to the rail 5 by means of two cams 11, 12 which engage with an opening 21 in the holder 8. The cams 11, 12 are driven by an electric motor 13. The pressing of the friction block 9 against the rail 5 ensues by means of compression springs 14. At its side facing the rail 5, the holder 8 includes a recess 17 lying between two oblique or ramp surfaces 15, 16, this recess 17 interacting with and engagable by a projection 18 secured to the rail 5.

In accord with FIG. 3, the cams 11, 12 have three working positions into which they can be rotated by the motor 13. In a first working position, the holder 8 with the friction block 9 is held at such a distance from the rail 5 that the carriage 4 is adjustable with complete freedom with respect to the rail 5. In a second work position, the holder 8 together with the friction block 9 is moved closer to the rail 5 so that the carriage 4 can still be manually adjusted with respect to the rail 5 but such that the projection 18 cammingly rides on surface 15 or 16 urging holder 8 away from the rail 5 against the bias of springs 14 and engages into the recess 17 when the projection 18 is traveled over and thus defines a corresponding exposure position. In this exposure position, then, a latching of the carriage 4 can ensue in a third work position of the cams 11, 12 in that the holder 8 is released to such degree that the compression springs 14 firmly press the friction block 9 against the rail 5.

In order to increase the spring bias when pressing the friction block 9 against the rail 5, a shaft 19 between the cams 11, 12 is likewise fashioned cam-like (FIG. 3) and is moved such by the motor 13 that a bearing plate 20 for the compression springs 14 is somewhat upwardly dislocated when cams 11, 12 are in the third work position and thus increases the tension of the compression springs 14.

In practice, various exposure positions are provided for the carriage 4. Each of these exposure positions has a projection at the rail 5 corresponding to the projection 18. An identical latch and interlock device is also provided between all rails 5, 7, so that a two-dimensional latching and interlocking of the carriage 4 is possible.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. A ceiling mount for an x-ray radiator comprising: a carriage carrying said x-ray radiator;

said carriage being displaceably guided by rails;
a friction block, motor-displaceable perpendicular to the rail direction, being attached to said carriage for locking said carriage to said rail at arbitrary locations;
said friction block being secured to a holder which is resiliently seated perpendicular to the corresponding rail;
said holder including a latch facing said allocated rail which resiliently interacts with corresponding latches on said rail for latching said carriage in specific latching positions at the points along said rail where said holder latch engages one of said rail latches.

2. A ceiling mount for an X-ray radiator comprising:
a carriage carrying said X-ray radiator;
said carriage being displaceably guided by rails;
a friction block, motor-displaceable perpendicular to the rail direction, being attached to said carriage for locking said carriage;
said friction block being secured to a holder which is resiliently seated perpendicular to the corresponding rail;
said holder including a latch facing said allocated rail which interacts with corresponding latches on said rail;
said holder being selectively movable between three positions by means of a motor, said holder latch being held away from said rail latch permitting free movement of said carriage on said rail in a first holder position, said holder being held sufficiently close to said rail to permit said rail latch to engage with said holder latch as said carriage is moved along said rail in a second holder position, and said friction block held in said holder being pressed against said rail in a third holder position to provide said latching of said carriage to said rail.

3. A ceiling mount according to claim 2, wherein said resilient latching is provided by springs allocated to said holder and said motor influences said springs for changing the spring tension.

4. A ceiling mount for an x-ray radiator comprising:
a carriage carrying said X-ray radiator;
at least one rail engagable by said carriage for guiding said carriage;
at least one friction block attached to said carriage being selectively movable into engagement with said rail for locking the carriage to said rail at arbitrary locations;
a holder for carrying said friction block;
said holder being movably mounted on said carriage toward and away from said rail;
said holder including a latch facing said rail and said rail including at least one latch facing said holder, said latches being selectively engagable to define a specific latching position at the point along said rail where said holder latch engages said rail latch.

5. A ceiling mount according to claim 4 including a motor for effecting movement of said holder toward and away from said rail.

6. A ceiling mount according to claim 4, wherein said movement of said holder is perpendicular to said rail.

7. A ceiling mount for an X-ray radiator comprising:
a carriage carrying said X-ray radiator;
at least one rail engagable by said carriage for guiding said carriage;
at least one friction block attached to said carriage being selectively movable into engagement with said rail for locking the carriage to said rail;
a holder for carrying said friction block;
said holder being movably mounted on said carriage toward and away from said rail;
said holder including a latch facing said rail and said rail including at least one latch facing said holder, said latches being selectively engagable to define a specific latching position at the point along said rail where said holder latch engages said rail latch;
said holder being selectively movable between three positions, wherein said holder latch is held away from said rail latch permitting free movement of said carriage on said rail in a first holder position, said holder is held sufficiently close to said rail to permit said rail latch to enage with said holder latch as said carriage is moved along said rail in a second holder position, and said friction block held in said holder is pressed against said rail in a third holder position to provide said latching of said carriage to said rail.

8. A ceiling mount according to claim 7, wherein said rail latch comprises a projection and said holder latch comprises a pair of ramped surfaces separated by a depression whereby said projection will engage said ramped surfaces upon a movement of said carriage on said rail past said rail latch with said carriage in said second position, said holder being resiliently mounted on said carriage such that said projection will ride on said ramped surfaces displacing said holder until said projection enters said depression where it will be captured preventing further movement of said carriage on said rail.

9. A ceiling mount according to claim 7 including a spring for biasing said holder towards said rail and further including motor driven cam members for urging said holder into said three positions against the bias of said spring.

* * * * *